US006665385B2

(12) United States Patent
Rogers et al.

(10) Patent No.: US 6,665,385 B2
(45) Date of Patent: Dec. 16, 2003

(54) MEDICAL MONITORING SYSTEM HAVING MULTIPATH COMMUNICATIONS CAPABILITY

(75) Inventors: Bobby E. Rogers, San Diego, CA (US); William R. Marable, Carlsbad, CA (US); Philip N. Eggers, Poway, CA (US)

(73) Assignee: Cardionet, Inc., San Diego, CA (US)

( * ) Notice: Subject to any disclaimer, the term of this patent is extended or adjusted under 35 U.S.C. 154(b) by 172 days.

(21) Appl. No.: 09/841,133

(22) Filed: Apr. 23, 2001

(65) Prior Publication Data

US 2002/0193076 A1 Dec. 19, 2002

(51) Int. Cl.[7] .............................................. H04M 11/00
(52) U.S. Cl. .............................. 379/106.02; 379/93.08; 128/903; 128/904
(58) Field of Search ....................... 379/106.02, 106.01, 379/90.01, 93.05–93.08, 93.28, 37, 38; 128/903, 904; 340/10.41, 573.4

(56) References Cited

U.S. PATENT DOCUMENTS

| 3,478,344 A | 11/1969 | Schwitzgebel et al. ...... 340/312 |
| 3,768,014 A | 10/1973 | Smith et al. ............. 324/158 R |
| 3,885,552 A | 5/1975 | Kennedy ............... 128/2.05 R |
| 3,902,478 A | 9/1975 | Konopasek et al. ..... 128/2.06 F |
| 3,925,762 A | 12/1975 | Keitlinger et al. ........... 340/150 |
| 4,173,971 A | 11/1979 | Karz ......................... 128/702 |
| 4,183,354 A | 1/1980 | Sibley et al. ................ 128/711 |
| 4,211,237 A | 7/1980 | Nagel ......................... 128/698 |
| 4,230,127 A | 10/1980 | Larson ........................ 128/706 |
| 4,241,237 A | 12/1980 | Paraskevakos et al. .. 179/2 AM |
| 4,457,315 A | 7/1984 | Bennish ...................... 128/704 |
| 4,531,527 A | 7/1985 | Reinhold, Jr. et al. ....... 128/696 |
| 4,535,783 A | 8/1985 | Marangoni ................. 128/711 |
| 4,598,272 A | 7/1986 | Cox ............................ 340/539 |
| 4,651,157 A | 3/1987 | Gray et al. .................. 342/457 |
| 4,675,656 A | 6/1987 | Narcisse ..................... 340/539 |
| 4,706,689 A | 11/1987 | Man ............................ 128/903 |
| 4,742,357 A | 5/1988 | Rackley ...................... 342/457 |
| 4,750,197 A | 6/1988 | Denekamp et al. ........... 379/58 |
| 4,777,478 A | 10/1988 | Hirsch et al. ............... 340/573 |
| 4,785,291 A | 11/1988 | Hawthorne ................. 340/573 |
| 4,819,860 A | 4/1989 | Hargrove et al. ........... 228/668 |
| 4,952,928 A | * 8/1990 | Carroll et al. ........... 340/10.41 |

(List continued on next page.)

FOREIGN PATENT DOCUMENTS

| DE | 4414 907 | 6/1995 |
| EP | 0 484 880 | 11/1991 |
| EP | 0 834 846 | 1/1996 |
| EP | 0 811 959 | 6/1997 |
| EP | 1 072 994 | 1/2001 |
| FR | 2 787 905 | 12/1998 |
| WO | WO 94/13197 | 6/1994 |
| WO | WO 96/25877 | 8/1996 |
| WO | WO 97/00708 | 1/1997 |
| WO | WO 99/44494 | 9/1999 |
| WO | WO 00/30529 | 6/2000 |
| WO | WO 00/62663 | * 10/2000 |

*Primary Examiner*—Wing Chan
(74) *Attorney, Agent, or Firm*—Fish & Richardson P.C.

(57) ABSTRACT

A medical monitoring system has a sensor system including a sensor associated with a patient and a remote monitoring unit. The remote monitoring unit includes a microprocessor in communication with the sensor system, and a portable-monitoring-unit transceiver system in communication with the microprocessor. The portable-monitoring-unit transceiver system has a land-line telephone transceiver and/or a cellular telephone transceiver, and a third-network transceiver such as a paging-network transceiver. A full data set is transmitted over the land-line telephone transceiver or the cellular telephone transceiver when communications links over these transceivers are available, and a reduced data set is transmitted over the third-network transceiver when communications links over the land-line telephone transceiver and the cellular telephone transceiver are not available.

21 Claims, 1 Drawing Sheet

U.S. PATENT DOCUMENTS

| | | | |
|---|---|---|---|
| 5,003,984 A | 4/1991 | Muraki et al. | 128/710 |
| 5,113,869 A | 5/1992 | Nappholz et al. | 128/696 |
| 5,172,698 A | 12/1992 | Stanko | 128/697 |
| 5,223,844 A | 6/1993 | Mansell et al. | 342/357 |
| 5,301,105 A | 4/1994 | Cummings, Jr. | 364/401 |
| 5,309,920 A | 5/1994 | Gallant et al. | 128/710 |
| 5,311,197 A | 5/1994 | Sorden et al. | 342/457 |
| 5,318,592 A | 6/1994 | Schaldach | 607/5 |
| 5,321,618 A | 6/1994 | Gessman | 364/413.06 |
| 5,334,974 A | 8/1994 | Simms et al. | 340/990 |
| 5,335,664 A | 8/1994 | Nagashima | 128/696 |
| 5,336,245 A | 8/1994 | Adams et al. | 607/32 |
| 5,348,008 A | 9/1994 | Bornn et al. | 128/642 |
| 5,389,934 A | 2/1995 | Kass | 342/357 |
| 5,394,879 A | 3/1995 | Gorman | 128/707 |
| 5,418,537 A | 5/1995 | Bird | 342/356 |
| 5,422,816 A | 6/1995 | Sprague et al. | 364/449 |
| 5,423,869 A | 6/1995 | Poore et al. | 607/18 |
| 5,458,123 A | 10/1995 | Unger | 128/696 |
| 5,461,365 A | 10/1995 | Schlager et al. | 340/573 |
| 5,470,233 A | 11/1995 | Fruchterman et al. | 434/112 |
| 5,479,482 A | 12/1995 | Grimes | 379/59 |
| 5,487,755 A | 1/1996 | Snell et al. | 607/27 |
| 5,497,149 A | 3/1996 | Fast | 340/988 |
| 5,503,158 A | 4/1996 | Coppock et al. | 128/696 |
| 5,504,491 A | 4/1996 | Chapman | 342/357 |
| 5,515,419 A | 5/1996 | Sheffer | 379/58 |
| 5,522,396 A | 6/1996 | Langer et al. | 128/696 |
| 5,544,661 A | 8/1996 | Davis et al. | 128/700 |
| 5,549,113 A | 8/1996 | Halleck et al. | 128/671 |
| 5,564,429 A | 10/1996 | Bornn et al. | 128/696 |
| 5,568,814 A | 10/1996 | Gallant et al. | 128/672 |
| 5,573,506 A | 11/1996 | Vasko | 604/65 |
| 5,576,952 A | 11/1996 | Stutman et al. | 364/413.02 |
| 5,579,775 A | 12/1996 | Dempsey et al. | 128/670 |
| 5,617,871 A | 4/1997 | Burrows | 128/696 |
| 5,620,472 A | 4/1997 | Rahbari | 607/27 |
| 5,626,624 A | 5/1997 | Schaldach et al. | 607/24 |
| 5,626,630 A | 5/1997 | Markowitz et al. | 607/60 |
| 5,629,678 A | 5/1997 | Gargano et al. | 340/573 |
| 5,649,303 A | 7/1997 | Hess et al. | 455/63 |
| 5,652,570 A | 7/1997 | Lepkofker | 340/573 |
| 5,678,562 A | 10/1997 | Sellers | 128/710 |
| 5,704,351 A | 1/1998 | Mortara et al. | 128/630 |
| 5,704,364 A | 1/1998 | Saltzstein et al. | 128/696 |
| 5,704,366 A | 1/1998 | Tacklind et al. | 128/716 |
| 5,713,856 A | 2/1998 | Eggers et al. | 604/65 |
| 5,720,770 A | 2/1998 | Nappholz et al. | 607/30 |
| 5,720,771 A | 2/1998 | Snell | 607/60 |
| 5,724,025 A | 3/1998 | Tavori | 340/573 |
| 5,729,197 A | 3/1998 | Cash | 340/539 |
| 5,730,143 A | 3/1998 | Schwarzberg | 128/710 |
| 5,731,757 A | 3/1998 | Layson, Jr. | 340/573 |
| 5,748,103 A | 5/1998 | Flach et al. | 340/870.07 |
| 5,749,367 A | 5/1998 | Gamlyn et al. | 128/696 |
| 5,749,907 A | 5/1998 | Mann | 607/27 |
| 5,752,976 A | 5/1998 | Duffin et al. | 607/32 |
| 5,759,199 A | 6/1998 | Snell et al. | 607/60 |
| 5,882,300 A | 3/1999 | Malinouskas et al. | 600/300 |
| 5,891,169 A | 4/1999 | Boheim et al. | 607/4 |
| 5,913,827 A | 6/1999 | Gorman | 600/509 |
| 5,913,881 A | 6/1999 | Benz et al. | 607/36 |
| 5,931,791 A | 8/1999 | Saltzstein et al. | 600/513 |
| 5,941,829 A | 8/1999 | Saltzstein et al. | 600/509 |
| 5,944,659 A | 8/1999 | Flach et al. | 600/300 |
| 5,950,110 A | 9/1999 | Hendrickson | 455/1 |
| 5,959,529 A | 9/1999 | Kail, IV | |
| 5,964,794 A | 10/1999 | Bolz et al. | 607/121 |
| 5,966,692 A | * 10/1999 | Langer et al. | 705/3 |
| 5,970,986 A | 10/1999 | Bolz et al. | 128/899 |
| 5,987,352 A | 11/1999 | Klein et al. | 600/509 |
| 5,987,519 A | 11/1999 | Peifer et al. | 709/230 |
| 6,026,008 A | 2/2000 | Feese | 365/63 |
| 6,038,469 A | 3/2000 | Karlsson et al. | 600/512 |
| 6,073,046 A | 6/2000 | Patel et al. | 600/509 |
| 6,083,248 A | 7/2000 | Thompson | 607/30 |
| 6,088,608 A | 7/2000 | Schulman et al. | 600/345 |
| 6,093,146 A | 7/2000 | Filangeri | 600/300 |
| 6,101,478 A | 8/2000 | Brown | 705/2 |
| 6,102,856 A | 8/2000 | Groff et al. | 600/301 |
| 6,154,674 A | 11/2000 | Meier | 607/23 |
| 6,160,478 A | 12/2000 | Jacobsen et al. | 340/539 |
| 6,181,966 B1 | 1/2001 | Nigam | 607/4 |
| 6,192,274 B1 | 2/2001 | Worzewski | 607/14 |
| 6,225,901 B1 | 5/2001 | Kail, IV | 340/539 |
| 6,245,092 B1 | 6/2001 | Schaldach, Jr. | 607/1 |
| 6,263,243 B1 | 7/2001 | Lang | 607/17 |
| 6,466,793 B1 | 10/2002 | Wallstedt et al. | 455/450 |
| 2002/0143576 A1 | 10/2002 | Nolvak et al. | |

* cited by examiner

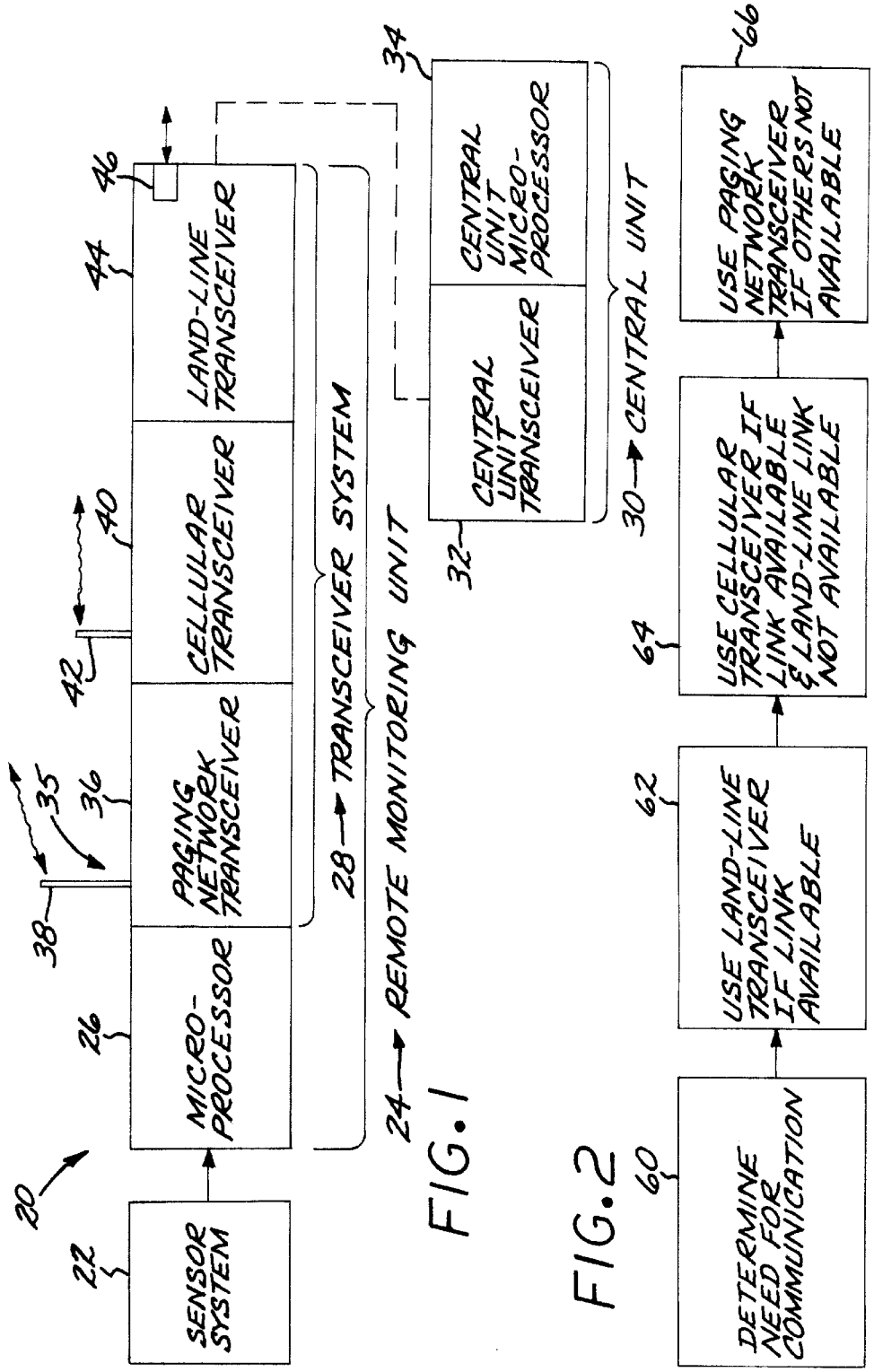

MEDICAL MONITORING SYSTEM HAVING MULTIPATH COMMUNICATIONS CAPABILITY

This invention relates to a medical monitoring system utilizing a remote monitoring unit and, more particularly, to the provision of a communication link for the remote monitoring unit with wider coverage than previously available.

BACKGROUND OF THE INVENTION

Advances in sensor technology, electronics, and communications have made it possible for physiological characteristics of patients to be monitored even when the patients are ambulatory and not in continuous, direct contact with a hospital monitoring system. For example, U.S. Pat. No. 5,959,529 describes a monitoring system in which the patient carries a remote monitoring unit with associated physiological sensors. The remote monitoring unit conducts a continuous monitoring of one or more physiological characteristics of the patient according to the medical problem of the patient, such as the heartbeat and its waveform.

An important objective of such portable monitoring systems is to establish contact with a central unit, which is in turn in contact with medical personnel and medical records. The ability to establish contact allows the central unit to determine the existence of a medical emergency with the patient, and to render medical assistance to the patient during such an emergency. The ability to establish contact is also important psychologically to the patient, so that the patient knows that (s)he is not alone and out of touch.

At the present time, the portable monitoring systems may establish communication links to the central unit through telephone land-lines, when the patient is in a location where land-line telephone access is readily available, or through the cellular telephone system when land-line access is not available or an emergency suddenly occurs. However, the present inventors have recognized that the existing medical monitoring systems are hampered by the fact that cellular telephone communication links are not available in many parts of the United States and in other countries. This unavailability arises because the cellular system infrastructure is not in place in relatively remote areas and because cellular telephone signals will not penetrate into many structures even if they are within the range of cellular telephone transceiver cell sites. The result is that the remote monitoring unit is unable to communicate with the central unit from many locations. The patient is therefore unable to obtain emergency assistance in those locations, and consequently feels isolated.

There is a need for an improved approach to ensuring wide-area communication availability for remote monitoring units of medical monitoring systems. The present invention fulfills this need, and further provides related advantages.

SUMMARY OF THE INVENTION

The present invention provides a medical monitoring system having a remote monitoring unit that has full communications coverage throughout the United States and much of the world. This communications coverage includes a wide geographical area and also locations such as the interiors of buildings that are sometimes unavailable for cellular telephone coverage. This full communications coverage allows the remote monitoring unit to communicate with the central unit under emergency conditions. Equally importantly, the patient being monitored has the peace of mind of knowing that (s)he is never completely out of touch with medical assistance. The present approach may be implemented relatively inexpensively, as the system infrastructure is in place and operating, and it may be adapted to new communications technologies that become available. The necessary addition to the remote monitoring unit adds very little in size, weight, and power consumption to the remote monitoring unit.

In accordance with the invention, a medical monitoring system comprises a sensor system including a sensor associated with a patient, and a remote monitoring unit. The remote monitoring unit comprises a microprocessor in communication with the sensor system, and a portable-monitoring-unit transceiver system in communication with the microprocessor. The portable-monitoring-unit transceiver system includes at least one transceiver selected from the group consisting of a land-line telephone transceiver and a primary wireless-network transceiver such as a cellular telephone transceiver, and preferably both. The portable-monitoring-unit transceiver system further comprises a third-network transceiver, such as a paging-network transceiver. Preferably, the portable-monitoring unit transceiver system includes a land-line telephone transceiver, a cellular telephone transceiver, and a paging-network transceiver.

The medical monitoring system also typically includes a central unit comprising a central unit transceiver which supports communication with the portable-monitoring-unit transceiver system.

The third network is preferably the paging system, but it may be of other types such as a marine network, an emergency network, or the like. The paging system, as it is used today in other applications, is intended to communicate relatively limited amounts of information, typically a brief message to a user that prompts the user to make some further contact or a short reply from the user. In a typical case, the user is prompted to go to a telephone to contact the person who has made the page. Stated alternatively, the paging network has a relatively low bandwidth. Within this constraint, however, the bidirectional paging network has the important advantage that it operates through orbiting communication satellites or an antenna system that give it very wide area coverage and at frequencies that permit its signal to penetrate to locations and to be used in locations that do not permit cellular communication. The paging network has the additional advantage that its infrastructure is in place and operating.

The present inventors have recognized that the use of the paging network for emergency medical monitor communications does not permit the transmission of as high a data rate as does cellular or land-line communication. However, in an emergency where high-bandwidth communication is not available, more limited communication between the patient and the central unit is better than no communication between the patient and the central unit.

Accordingly, in this architecture the microprocessor of the remote monitoring unit usually includes a first processing routine that transmits a full data set over the land line or cellular system when a communication link over one of these transceivers is available, and a second processing routine that transmits a reduced data set over the paging-network (or other third-network) transceiver when a communication link over other transceivers is not available. For example, the first processing routine transmits full physiological information such as a complete heartbeat waveform in the case of heart patients, while the second processing routine might transmit a reduced data set such as heart rate, waveform classification, and other computed information locally derived from the heartbeat waveform by calculations made in the remote monitoring unit. Alternatively, the remote monitoring unit may make multiple transmissions over the paging network, but even in this case it is unlikely that full physiological information from the sensor can be transmitted at the same rate as achieved over the land-line or cellular communication systems.

The present invention establishes a communications hierarchy for the medical monitoring system. The medical monitoring system preferably has two basic communications paths between the remote monitoring unit and the central unit, the land-line telephone system and a wireless link such as the cellular-network system. Each of these communications paths has a relatively high communications bandwidth and can carry extensive data. However, in those cases where the basic communications system is unavailable, a third-network backup system, usually with a much narrower bandwidth, provides a minimal data set to define the event detected.

Other features and advantages of the present invention will be apparent from the following more detailed description of the preferred embodiment, taken in conjunction with the accompanying drawings, which illustrate, by way of example, the principles of the invention. The scope of the invention is not, however, limited to this preferred embodiment.

BRIEF DESCRIPTION OF THE DRAWINGS

FIG. 1 is a schematic diagram of a medical monitoring system; and

FIG. 2 is a block flow diagram of a method of operation of the communications.

DETAILED DESCRIPTION OF THE INVENTION

FIG. 1 depicts a preferred embodiment of a medical monitoring system 20. The medical monitoring system 20 includes a sensor system 22 having a sensor associated with a patient. The sensor system 22 may monitor any of a variety of physiological characteristics of the patient, such as a heartbeat waveform, blood pressure, brain signals, blood chemistry, and the like. The sensor system 22 communicates with a remote monitoring unit (RMU) 24 that is either carried by the patient or is relatively physically close to the patient. The communication between the sensor system 22 and the remote monitoring unit 24 may be either wired or wireless, such as a short-range radio frequency link.

The remote monitoring unit 24 includes a microprocessor 26 in communication with the sensor system 22. The microprocessor 26 performs computations as may be necessary and oversees the operation of a portable-monitoring-unit transceiver system 28 that is also a part of the remote monitoring unit 24. The portable-monitoring-unit transceiver system 28 communicates with a central unit (CU) 30 having a central-unit transceiver system 32 that supports communications of the types found in the portable-monitoring-unit transceiver system 28 and which will be discussed subsequently. The central unit 30 also includes a central unit microprocessor 34 that coordinates the central-unit transceiver system 32 and performs other analytical and control functions. The general features of a preferred form of the medical monitoring system 20, other than those to be discussed subsequently, are described in U.S. Pat. No. 5,959,529, whose disclosure is incorporated by reference.

The portable-monitoring-unit transceiver system 28 includes a third-network transceiver 35. The third-network transceiver 35 is preferably a two-way paging-network transceiver operable with the paging network, and the following discussion will focus on that preferred embodiment. However, the third-network transceiver 35 may be of other backup types, such as a specialized emergency-network transceiver, a marine-network transceiver, and the like.

The embodiment of FIG. 1 includes the paging network transceiver 36 and its antenna 38 that selectively establish a third-network link (in this case a paging-network link) with the central unit 30. The paging network transceiver 36 operates using the existing paging network available throughout the United States and much of the rest of the world. Communication with the paging network is available in virtually every part of the United States and in most parts of the rest of the world. It is available in the open, inside buildings, in aircraft, and onboard ships. The paging network originally operated unidirectionally, with signals conveyed only from the satellite to the paging unit, but it is now available in a bidirectional form as suggested by the term "transceiver", an art-recognized contraction of "transmitter/receiver". That is, the bidirectional paging transceiver 36 may either receive information or send information, via the existing paging system, to the central unit transceiver 32.

The portable-monitoring-unit transceiver system 28 further includes a cellular telephone transceiver 40 and its antenna 42, which serves as a primary wireless-network transceiver. The cellular transceiver 40 selectively establishes a cellular link with the central unit 30. The cellular telephone transceiver 36 operates using the existing network of cell sites available through much of the United States and some of the rest of the world. Cellular communications links are operable in the open, inside most automobiles within range of cell sites, and inside many buildings, but are often not available in some buildings, in aircraft, or onboard ships. The cellular telephone transceiver 40 may either receive information or send information through the cellular network to the central unit transceiver 32.

The portable-monitoring-unit transceiver system 28 further includes a land-line telephone transceiver 44 and its plug jack 46. The land-line telephone transceiver 44 selectively establishes a land-line link with the central unit 30. The land-line telephone transceiver 44 operates using the land-line system (which may also include microwave links of the land lines) available through much of the United States and much of the rest of the world. Land-line telephone communications links are available through telephone central switching offices wherever there is a plug connection, but the need for physical access to a plug limits the mobility of the patient. The land-line telephone transceiver 44 may either receive information or send information through the land-line system to the central unit transceiver 32.

FIG. 2 depicts the sequence of events when communication is required between the remote monitoring unit 24 and the central unit 30. A need for communications is first determined, numeral 60. This step typically occurs when the remote monitoring unit 24 determines that it needs to communicate with the central unit 30, but it may also occur when the central unit 30 determines that it needs to communicate with the remote monitoring unit 24. The former case will be discussed in detail, but the discussion is equally applicable to the latter case.

The land-line transceiver 44 is used if the land-line link is available, numeral 62. That is, the microprocessor 26 seeks to open a land-line communication link to the central unit 30 through the land-line transceiver 44. If there is no plug in the plug jack 46 or if it is otherwise not possible to dial up the central unit 30, then the microprocessor 26 seeks to open a cellular link to the central unit 30 through the cellular telephone transceiver 40, numeral 64. The use of the land-line transceiver 44 is preferred to the use of the cellular telephone transceiver 40, because the land-line communication link is more reliable, more secure, and usually less costly, if available.

If the communication link is established either through the land-line transceiver 44 or the cellular transceiver 40, then the microprocessor 26 uses a first processing routine stored therein that transmits a full data set through either of these wide-bandwidth communications channels. This is the desired operating mode of the medical monitoring system 20, because its full data capabilities may be employed.

However, as noted above, in some instances neither the land-line link nor the cellular link is available due to reasons such as unavailability of the land line, unavailability of the cellular system, user overload of the cellular system, interference to wireless communications in the frequency band of the cellular system, or the like. In that case, the paging-network (or other third-network) transceiver 36 is used, numeral 66. Because of the narrow communications bandwidth of the paging network, the microprocessor 26 typically uses a second processing routine stored therein that determines and transmits a reduced data set over the paging-network link. In some cases where the sensor system 22 obtains a small amount of data such as a single blood chemistry number, the full data set may be transmitted over the paging network transceiver 36. In other cases where the sensor system 22 obtains much larger amounts of data, such as a heartbeat waveform, then it is not possible to transmit the full data set even if data compression techniques are used. The second processing routine is written to select only the most important of the data that is gathered by the sensor system 22, or to calculate secondary data from the gathered data, for transmission over the paging network transceiver 36. In the case of the heartbeat, for example, the second processing routine may calculate a heart rate (number of beats per minute), an amplitude, and waveform characteristics of selected portions of the full heartbeat signal for transmission within the bandwidth constraints of the paging network. The second processing routine would typically not select voice or other audio signals for transmission. This reduced data set, while not as complete as the full data set, is far better and more useful to the central unit 30 in diagnosing and aiding the patient than having no information and no contact at all. It is possible to perform multiple serial communications between the remote monitoring unit 24 and the central unit 30 to transmit more information, but even in that case it is unlikely that the full data set can be conveyed. The selection of the content of the reduced data set and thence the content of the second processing routine is left to the individual situation and type of data being monitored for the individual patient.

The present invention provides a communications hierarchy based upon a recognition that limited communications is better than no communications in many instances, and a recognition of the tradeoff between communications availability and bandwidth. Some currently available communications links are summarized in the following table, with the land-line telephone being a wired connection and the other communications links being wireless. However, it is emphasized that the use of the present invention is not limited to these types of communications links and includes other presently available and future communications links:

| Communications Link | Center Frequency (MHZ) | Bandwidth (Qualitative) |
| --- | --- | --- |
| Land-line telephone | — | very high |
| Analog cellular phone | 859 | moderate |
| Digital CDMA cellular phone | 800 | high |
| Digital PCS CDMA cellular phone | 1900 | high |
| Motorola Reflex paging | 900 | moderate |
| Celemetry paging | 859 | very low |

Thus, it is preferred that the portable-monitoring-unit transceiver system of the medical monitoring system include the land-line telephone transceiver and a digital cellular transceiver. However, when communication over these communications links is not available, one of the paging systems may be used as a backup. Even data communications over a low-bandwidth or moderate-bandwidth paging system is preferable to no communication in many situations.

Although a particular embodiment of the invention has been described in detail for purposes of illustration, various modifications and enhancements may be made without departing from the spirit and scope of the invention. Accordingly, the invention is not to be limited except as by the appended claims.

What is claimed is:

1. A medical monitoring system, comprising:
   a sensor system including a sensor associated with a patient;
   a remote monitoring unit comprising
      a microprocessor in communication with the sensor system, and
      a portable-monitoring-unit transceiver system in communication with the microprocessor, the portable-monitoring-unit transceiver system comprising
         a land-line telephone transceiver,
         a primary wireless-network transceiver, and
         a third-network transceiver; and
      the microprocessor includes a processing routine that transmits a data set matches the available communication link.

2. The medical monitoring system of claim 1, wherein the primary wireless-network transceiver comprises a cellular telephone transceiver.

3. The medical monitoring system of claim 1, wherein the third-network transceiver comprises a paging-network transceiver.

4. The medical monitoring system of claim 1, wherein the third-network transceiver comprises a bidirectional paging-network transceiver.

5. The medical monitoring system of claim 1, wherein a third network operating with the third-network transceiver has a lower data bandwidth than a primary wireless network operating with the primary wireless-network transceiver.

6. The medical monitoring system of claim 1, wherein the medical monitoring system further includes:
   a central unit comprising:
      a central unit transceiver which supports communication with the portable-monitoring-unit transceiver system.

7. The medical monitoring system of claim 1, wherein the microprocessor of the remote monitoring unit includes:
   a first processing routine that transmits
      a full data set over the land-line telephone transceiver when a communication link over the land-line telephone transceiver is available, and a full data set over the primary wireless-network transceiver when a communication link over the primary wireless-network transceiver is available and a communication link over the land-line telephone transceiver is not available, and a second processing routine that transmits a reduced data set over the third-network transceiver when a communication link over the land-line telephone transceiver and the primary wireless-network transceiver are not available.

8. A medical monitoring system, comprising:

a sensor system including a sensor associated with a patient;

a remote monitoring unit comprising
 a microprocessor in communication with the sensor system, and
 a portable-monitoring-unit transceiver system in communication with the microprocessor, the portable-monitoring-unit transceiver system comprising a paging-network transceiver, wherein the microprocessor includes a processing routine that transmits a data set that matches the available communication link.

9. The medical monitoring system of claim 8, wherein the medical monitoring system further includes:

a central unit comprising:
 a central unit transceiver which supports communication with the portable-monitoring-unit transceiver system.

10. A medical monitoring system, comprising:

a sensor system including a sensor associated with a patient;

a remote monitoring unit comprising
 a microprocessor in communication with the sensor system, and
 a portable-monitoring-unit transceiver system in communication with the microprocessor, the portable-monitoring-unit transceiver system comprising
  at least one transceiver selected from the group consisting of a land-line telephone transceiver and a primary wireless-network transceiver, and
  a third-network transceiver; and
 the microprocessor includes a processing routine that transmits a data set that matches the available communication link.

11. The medical monitoring system of claim 10, wherein the primary wireless-network transceiver comprises a cellular telephone transceiver.

12. The medical monitoring system of claim 10, wherein the third-network transceiver comprises a paging-network transceiver.

13. The medical monitoring system of claim 10, wherein the medical monitoring system further includes:

a central unit comprising:
 a central unit transceiver which supports communication with the portable-monitoring-unit transceiver system.

14. The medical monitoring system of claim 10, wherein the microprocessor of the remote monitoring unit includes:

a first processing routine that transmits a full data set over the at least one transceiver when a communication link over the at least one transceiver is available, and a second processing routine that transmits a reduced data set over the third-network transceiver when a communication link over the at least one additional transceiver is not available.

15. A method for performing communications by a remote monitoring unit to a central unit, comprising the steps of:

determining a need far communication by the remote monitoring unit to the central unit;

the remote monitoring unit communicating with the central unit by a land-line link if the land-line link is available;

the remote monitoring unit communicating with the central unit by a cellular link if the land-line link is not available;

the remote monitoring unit communicating with the central unit by a third-network link if the land-line link and the cellular link are not available; and wherein a data set is transmitted from the remote monitoring unit to the central unit that matches the available communication link.

16. The method of claim 15, wherein the third-network link is a paging-network link.

17. The method for performing communications by a remote monitoring unit to a central unit, comprising the steps of:

determining a need for communication by the remote monitoring unit to the central unit;

the remote monitoring unit determining the available communication link; and the remote monitoring unit matching a data set to be sent to the central unit based upon the available communication link.

18. The method of claim 17, wherein the remote monitoring unit attempts to establish a communication link with the central unit by at least one of a land-line link, a cellular link or a third-network link.

19. The method of claim 18, wherein the third network link is a paging network link.

20. A medical monitoring system, comprising:

a sensor system including a sensor associated with a patient;

a remote monitoring unit comprising
 a microprocessor in communication with the sensor system, and
 a portable-monitoring-unit transceiver system in communication with the microprocessor, the portable-monitoring-unit transceiver system comprising
  land-line telephone transceiver,
  a primary wireless-network transceiver, and
  a third-network transceiver; and a first processing routine that transmits
 a full data set over the land-line telephone transceiver when a communication link over the land-line transceiver is available; and
 a full data set over the primary wireless-network transceiver when a communication link over the primary wireless-network transceiver is available and a communication link over the land-line telephone transceiver is not available; and a second processing routine that transmits a reduced data set over the third-network transceiver when a communication link over the land-line telephone transceiver and the primary wireless-network transceiver are not available.

21. A medical monitoring system, comprising:

a sensor system including a sensor associated with a patient;

a remote monitoring unit comprising
- a microprocessor in communication with the sensor system, and
- a portable-monitoring-unit transceiver system in communication with the microprocessor, the portable-monitoring-unit transceiver system comprising
  - at least one transceiver selected from the group consisting of a land-line telephone transceiver and a primary wireless-network transceiver, and
  - a third-network transceiver; and
- a first processing routine that transmits a full data set over the at least one transceiver when a communication link over the at least one transceiver is available; and
- a second processing routine that transmits a reduced data set over the third-network transceiver when a communication link over the at least one additional transceiver is not available.

* * * * *